(12) United States Patent
Marmo (10) Patent No.: US 7,585,075 B2
(45) Date of Patent: Sep. 8, 2009

(54) CORNEAL ONLAYS AND WAVEFRONT ABERRATION CORRECTION TO ENHANCE VISION

(75) Inventor: J. Christopher Marmo, Danville, CA (US)

(73) Assignee: ForSight Labs, LLC, Menlo Park, CA (US)

( * ) Notice: Subject to any disclaimer, the term of this patent is extended or adjusted under 35 U.S.C. 154(b) by 0 days.

(21) Appl. No.: 11/881,727

(22) Filed: Jul. 27, 2007

(65) Prior Publication Data

US 2008/0024723 A1    Jan. 31, 2008

Related U.S. Application Data

(63) Continuation of application No. 11/128,824, filed on May 13, 2005, now abandoned.

(60) Provisional application No. 60/573,657, filed on May 20, 2004.

(51) Int. Cl.
*A61B 3/00* (2006.01)
*A61B 3/10* (2006.01)

(52) U.S. Cl. .................. 351/219; 351/246; 351/205

(58) Field of Classification Search .......... 351/205–246
See application file for complete search history.

(56) References Cited

U.S. PATENT DOCUMENTS

| | | | |
|---|---|---|---|
| 4,078,564 A | 3/1978 | Spina et al. | |
| 4,126,904 A | 11/1978 | Shepard | |
| 4,223,984 A | 9/1980 | Miyata et al. | |
| 4,268,131 A | 5/1981 | Miyata et al. | |
| 4,346,482 A | 8/1982 | Tennant et al. | |
| 4,452,235 A | 6/1984 | Reynolds | |
| 4,452,776 A | 6/1984 | Refojo | |
| 4,452,925 A | 6/1984 | Kuzma et al. | |
| 4,563,779 A | 1/1986 | Kelman | |
| 4,581,030 A | 4/1986 | Bruns et al. | |
| 4,600,533 A | 7/1986 | Chu | |
| 4,619,657 A | 10/1986 | Keates et al. | |
| 4,621,912 A | 11/1986 | Meyer | |
| 4,624,669 A | 11/1986 | Grendahl | |

(Continued)

FOREIGN PATENT DOCUMENTS

| | | |
|---|---|---|
| CA | 2227827 | 7/1999 |
| DE | 199 47 711 | 5/2001 |
| EP | 0 387 975 | 3/1990 |
| EP | 1 530 600 B1 | 5/2005 |
| EP | 1 741 457 A1 | 1/2007 |

(Continued)

OTHER PUBLICATIONS

Dr. Michael Cox and Mr. Holger Dietze, "Correcting Ocular Wavefront Aberrations using Contact Lenses", University of Bradford, Website: optometry-webmanager@bradford.ac.uk. , Last modified Oct. 7, 2003.

Nader, N., *Ocular Surgery News*, "Learning a new language: understanding the terminology of wavefront-guided ablation", Feb. 1, 2003.

U.S. Appl. No. 10/661,400, filed Sep. 12, 2003.

(Continued)

*Primary Examiner*—Mohammed Hasan
(74) *Attorney, Agent, or Firm*—Townsend and Townsend and Crew LLP (57) ABSTRACT

Devices and methods for improving vision are described. The vision of a person can be corrected using a corneal onlay or a lens positioned between an epithelial cell layer and Bowman's membrane of the person's eye. Wavefront aberrations are measured for the person's eye or eyes, and the aberrations are used to shape the corneal onlay to provide a desired vision correction power, or to shape the person's cornea.

24 Claims, 1 Drawing Sheet

U.S. PATENT DOCUMENTS

| | | | |
|---|---|---|---|
| 4,636,210 A | 1/1987 | Hoffer | |
| 4,655,774 A | 4/1987 | Choyce | |
| 4,655,980 A | 4/1987 | Chu | |
| 4,676,790 A | 6/1987 | Kern | |
| 4,689,399 A | 8/1987 | Chu | |
| 4,693,715 A | 9/1987 | Abel, Jr. | |
| 4,715,858 A | 12/1987 | Lindstrom | |
| 4,725,671 A | 2/1988 | Chu et al. | |
| 4,780,409 A | 10/1988 | Monji et al. | |
| 4,784,485 A | 11/1988 | Ho | |
| 4,799,931 A | 1/1989 | Lindstrom | |
| 4,810,082 A | 3/1989 | Abel, Jr. | |
| 4,819,617 A | 4/1989 | Goldberg et al. | |
| 4,834,748 A | 5/1989 | McDonald | |
| 4,851,003 A | 7/1989 | Lindstrom | |
| 4,923,467 A | 5/1990 | Thompson | |
| 4,952,212 A | 8/1990 | Booth et al. | |
| 4,959,353 A | 9/1990 | Brown et al. | |
| 4,973,493 A | 11/1990 | Guire | |
| 4,978,713 A | 12/1990 | Goldenberg | |
| 4,979,959 A | 12/1990 | Guire | |
| 4,981,841 A | 1/1991 | Gibson | |
| 4,983,181 A * | 1/1991 | Civerchia | 351/160 H |
| 4,994,081 A | 2/1991 | Civerchia | |
| 5,019,097 A | 5/1991 | Knight et al. | |
| 5,044,743 A | 9/1991 | Ting | |
| 5,104,408 A | 4/1992 | Thompson | |
| 5,108,428 A | 4/1992 | Capecchi et al. | |
| 5,112,350 A | 5/1992 | Civerchia | |
| 5,114,627 A | 5/1992 | Civerchia | |
| 5,151,310 A | 9/1992 | Yanagisawa et al. | |
| 5,156,622 A | 10/1992 | Thompson | |
| 5,163,956 A * | 11/1992 | Liu et al. | 623/4.1 |
| 5,171,318 A | 12/1992 | Gibson et al. | |
| 5,192,316 A | 3/1993 | Ting | |
| 5,196,026 A | 3/1993 | Barrett et al. | |
| 5,196,027 A | 3/1993 | Thompson et al. | |
| 5,201,764 A | 4/1993 | Kelman et al. | |
| 5,213,720 A | 5/1993 | Civerchia | |
| 5,244,799 A | 9/1993 | Anderson | |
| 5,263,992 A | 11/1993 | Guire | |
| 5,288,436 A | 2/1994 | Liu et al. | |
| 5,292,514 A | 3/1994 | Capecchi et al. | |
| 5,300,118 A | 4/1994 | Silvestrini et al. | |
| 5,330,911 A | 7/1994 | Hubbell et al. | |
| 5,401,508 A | 3/1995 | Manesis | |
| 5,433,745 A | 7/1995 | Graham et al. | |
| 5,443,473 A | 8/1995 | Miller et al. | |
| 5,470,831 A | 11/1995 | Whitman et al. | |
| 5,475,052 A | 12/1995 | Rhee et al. | |
| 5,489,300 A | 2/1996 | Capecchi et al. | |
| 5,496,339 A | 3/1996 | Koepnick | |
| 5,522,888 A | 6/1996 | Civerchia | |
| 5,547,468 A | 8/1996 | Simon et al. | |
| 5,552,452 A | 9/1996 | Khadem et al. | |
| 5,565,519 A | 10/1996 | Rhee et al. | |
| 5,587,175 A | 12/1996 | Viegas et al. | |
| 5,614,587 A | 3/1997 | Rhee et al. | |
| 5,632,773 A | 5/1997 | Graham et al. | |
| 5,690,657 A | 11/1997 | Koepnick | |
| 5,713,957 A | 2/1998 | Steele et al. | |
| 5,716,633 A | 2/1998 | Civerchia | |
| 5,722,971 A | 3/1998 | Peyman | |
| 5,744,545 A | 4/1998 | Rhee et al. | |
| 5,800,541 A | 9/1998 | Rhee et al. | |
| 5,827,641 A | 10/1998 | Parenteau et al. | |
| 5,832,313 A | 11/1998 | Ishibashi et al. | |
| 5,836,313 A | 11/1998 | Perez et al. | |
| 5,919,185 A | 7/1999 | Peyman | |
| 5,964,748 A | 10/1999 | Peyman | |
| 5,994,133 A | 11/1999 | Meijs et al. | |
| 6,015,609 A | 1/2000 | Chaouk et al. | |
| 6,030,634 A | 2/2000 | Wu et al. | |
| 6,055,990 A | 5/2000 | Thompson | |
| 6,060,530 A | 5/2000 | Chaouk et al. | |
| 6,063,073 A | 5/2000 | Peyman | |
| 6,071,293 A | 6/2000 | Krumeich | |
| 6,086,204 A | 7/2000 | Magnante | |
| 6,090,995 A | 7/2000 | Reich et al. | |
| 6,103,528 A | 8/2000 | An et al. | |
| 6,165,488 A | 12/2000 | Tardy et al. | |
| 6,186,148 B1 | 2/2001 | Okada | |
| 6,197,019 B1 | 3/2001 | Peyman | |
| 6,203,538 B1 | 3/2001 | Peyman | |
| 6,217,571 B1 | 4/2001 | Peyman | |
| 6,221,067 B1 | 4/2001 | Peyman | |
| 6,271,278 B1 | 8/2001 | Park et al. | |
| 6,280,470 B1 | 8/2001 | Peyman | |
| 6,284,537 B1 | 9/2001 | Offord et al. | |
| 6,323,278 B2 | 11/2001 | Rhee et al. | |
| 6,335,006 B1 | 1/2002 | Miller et al. | |
| 6,361,560 B1 | 3/2002 | Nigam | |
| 6,384,105 B1 | 5/2002 | He et al. | |
| 6,388,047 B1 | 5/2002 | Won et al. | |
| 6,454,800 B2 | 9/2002 | Dalton et al. | |
| 6,454,802 B1 | 9/2002 | Bretton et al. | |
| 6,511,949 B1 | 1/2003 | Nitta et al. | |
| 6,544,286 B1 | 4/2003 | Perez | |
| 6,547,391 B2 | 4/2003 | Ross, III et al. | |
| 6,551,307 B2 | 4/2003 | Peyman | |
| 6,566,406 B1 | 5/2003 | Pathak et al. | |
| 6,579,918 B1 | 6/2003 | Auten et al. | |
| 6,585,375 B2 * | 7/2003 | Donitzky et al. | 351/219 |
| 6,607,522 B1 | 8/2003 | Hamblin et al. | |
| 6,645,715 B1 | 11/2003 | Griffith et al. | |
| 6,689,165 B2 | 2/2004 | Jacob et al. | |
| 6,702,807 B2 | 3/2004 | Peyman | |
| 6,717,651 B2 * | 4/2004 | Kato et al. | 355/55 |
| 6,855,163 B2 | 2/2005 | Peyman | |
| 6,880,558 B2 | 4/2005 | Perez | |
| 6,897,064 B2 | 5/2005 | Yoshioka et al. | |
| 6,918,904 B1 | 7/2005 | Peyman | |
| 7,004,953 B2 | 2/2006 | Pallikaris et al. | |
| 7,053,051 B2 | 5/2006 | Pallikaris et al. | |
| 7,077,839 B2 | 7/2006 | Hamblin et al. | |
| 7,156,859 B2 | 1/2007 | Pallikaris et al. | |
| 7,166,118 B2 | 1/2007 | Dame et al. | |
| 7,207,998 B2 | 4/2007 | Feingold | |
| 2001/0018612 A1 | 8/2001 | Carson et al. | |
| 2001/0027314 A1 | 10/2001 | Peyman | |
| 2001/0034516 A1 | 10/2001 | Peyman | |
| 2001/0047203 A1 | 11/2001 | Dalton et al. | |
| 2002/0022013 A1 | 2/2002 | Leukel et al. | |
| 2002/0039788 A1 | 4/2002 | Isseroff et al. | |
| 2002/0052596 A1 | 5/2002 | Pallikaris et al. | |
| 2002/0052615 A1 | 5/2002 | Ross et al. | |
| 2002/0055753 A1 | 5/2002 | Silvestrini | |
| 2002/0065555 A1 | 5/2002 | Nigam | |
| 2002/0071097 A1 | 6/2002 | Ross, III et al. | |
| 2002/0138069 A1 | 9/2002 | Peyman | |
| 2003/0018123 A1 | 1/2003 | Bagrov et al. | |
| 2003/0018347 A1 | 1/2003 | Pallikaris et al. | |
| 2003/0018348 A1 | 1/2003 | Pallikaris et al. | |
| 2003/0093083 A1 | 5/2003 | Peyman | |
| 2003/0105521 A1 | 6/2003 | Perez | |
| 2003/0220653 A1 * | 11/2003 | Perez | 606/107 |
| 2004/0015234 A1 | 1/2004 | Peyman | |
| 2004/0046287 A1 * | 3/2004 | Andino et al. | 264/401 |
| 2004/0075807 A1 * | 4/2004 | Ho et al. | 351/160 R |
| 2004/0125459 A1 * | 7/2004 | Tanitsu et al. | 359/619 |
| 2004/0142038 A1 | 7/2004 | Echols et al. | |
| 2004/0170666 A1 | 9/2004 | Keates et al. | |
| 2004/0183998 A1 | 9/2004 | Luce | |
| 2004/0243160 A1 | 12/2004 | Shiuey et al. | |

| | | | |
|---|---|---|---|
| 2005/0070942 | A1 | 3/2005 | Perez |
| 2005/0080484 | A1 | 4/2005 | Marmo et al. |
| 2005/0124982 | A1 | 6/2005 | Perez |
| 2005/0196427 | A1 | 9/2005 | Tirrell et al. |
| 2005/0251185 | A1 | 11/2005 | Gebauerl |
| 2005/0259221 | A1 | 11/2005 | Marmo |
| 2006/0034807 | A1 | 2/2006 | Griffith |
| 2006/0052796 | A1 | 3/2006 | Perez et al. |
| 2006/0064112 | A1 | 3/2006 | Perez |
| 2006/0071356 | A1* | 4/2006 | Beebe ........................ 264/2.2 |
| 2006/0134050 | A1 | 6/2006 | Griffith et al. |
| 2006/0134170 | A1 | 6/2006 | Griffith et al. |
| 2006/0190004 | A1 | 8/2006 | Dick et al. |
| 2006/0241751 | A1 | 10/2006 | Marmo et al. |
| 2006/0246113 | A1 | 11/2006 | Griffith et al. |
| 2006/0247660 | A1 | 11/2006 | Perez |
| 2007/0016292 | A1 | 1/2007 | Perez |
| 2007/0026046 | A1 | 2/2007 | Fogg et al. |
| 2007/0182920 | A1 | 8/2007 | Back et al. |
| 2007/0239184 | A1 | 10/2007 | Gaeckle et al. |
| 2007/0265649 | A1 | 11/2007 | Perez |
| 2008/0269119 | A1 | 10/2008 | Griffith |

FOREIGN PATENT DOCUMENTS

| | | |
|---|---|---|
| GB | 1 569 707 | 6/1980 |
| GB | 2305608 | 4/1997 |
| WO | WO 88/02622 | 4/1988 |
| WO | WO 92/14420 | 9/1992 |
| WO | WO 93/07889 | 4/1993 |
| WO | WO 94/16570 | 8/1994 |
| WO | WO 94/17851 | 8/1994 |
| WO | WO 95/13764 | 5/1995 |
| WO | WO 98/03267 | 1/1998 |
| WO | WO 98/31316 | 7/1998 |
| WO | WO 99/37752 | 7/1999 |
| WO | WO 00/07525 | 2/2000 |
| WO | WO 00/35524 | 6/2000 |
| WO | WO 00/67694 | 11/2000 |
| WO | WO 02/06883 A2 | 1/2002 |
| WO | WO 02/092142 | 11/2002 |
| WO | WO 02/092142 A3 | 11/2002 |
| WO | WO 2004/014969 | 2/2004 |
| WO | WO 2004/015090 | 2/2004 |
| WO | WO 2004/024035 | 3/2004 |
| WO | WO 2004/028356 | 4/2004 |
| WO | WO 2004/052254 | 6/2004 |
| WO | WO 2005/030102 | 4/2005 |
| WO | WO 2005/042043 | 5/2005 |
| WO | WO 2005/049071 A2 | 6/2005 |
| WO | WO 2005/116729 | 12/2005 |
| WO | WO 2006/007408 | 1/2006 |
| WO | WO 2006/015490 | 2/2006 |
| WO | WO 2006/020859 A2 | 2/2006 |
| WO | WO 2006/116601 | 11/2006 |
| WO | WO 2006/116732 | 11/2006 |
| WO | WO 2007/028258 | 3/2007 |

OTHER PUBLICATIONS

"Licensing agreement for automated microkeratome-based device" found online at: http://www.optical-world.co.uk/Aug%202002%20international_outlook.htm. no author given, printed on Sep. 13, 2002.

Ahmed et al., "Characterization and inhibition of fibrin hydrogel-degrading enzymes during development of tissue engineering scaffolds," Tissue Eng. Jul. 2007;13(7):1469-77.

Biowski et al., "Corneal Lathing Using the Excimer Laser and a Computer-controlled Positioning System," J Refract Surg. Jan.-Feb. 2000;16(1):23-31.

Bissen-Miyajima, "At issue: the next generation of microkeratomes", Ocular Surgery news Europe! Asia.Pacific edition, Feb. 2002, 4 pages total. Downloaded from the Internet: << http://www.osnsupersite.com/view.aspx?rid=14685>>.

Blais et al., "LBP and CD14 secreted in tears by the lacrimal glands modulate the LPS response of corneal epithelial cells," Invest Ophthalmol Vis Sci. Nov. 2005;46(11):4235-44.

Bloomfield et al., "The use of Eastman 910 monomer as an adhesive in ocular surgery. I. Biologic effects on ocular tissues," Am J Ophthalmol. Apr. 1963;55:742-748.

Bonatti et al., "A fibrin-related line of research and theoretical possibilities for the use of fibrin glue as a temporary basal membrane in non-perforated corneal ulcers and in photorefractive keratectomy (PRK)-operated corneas," Arq Bras Oftalmol. Sep.-Oct. 2007;70(5):884-889.

Bourne, "Clinical estimation of corneal endothelial pump function," Trans Am Ophthalmol Soc. 1998; 96: 229-242.

Burrill, "Gel-Assisted Lasek", Cataract & Refractive Surgery Today, no date given. 3 pages total. Downloaded from the Internet: <<http://http://www.crstodayarchive.com/03_archive/0402/crst0402_19.html>>.

Carlsson et al., "Bioengineered corneas: how close are we?" Curr Opin Ophthalmol. Aug. 2003;14(4):192-197.

Ciba Vision website, "research and development" "Sub-epithelial Separator", before year 2003, 1 page total.

Controlled Release Society Newsletter, 2005; 22(2): 1-36.

Delustro et al., "A comparative study of the biologic and immunologic response to medical devices derived from dermal collagen," J Biomed Mater Res. Jan. 1986;20(1):109-120.

Dohlman et al., "Further experience with glued-on contact lens (artificial epithelium)," Arch Ophthalmol. Jan. 1970;83(1):10-20.

Dohlman et al., "Replacement of the corneal epithelium with a contact lens (artificial epithelium)," Trans Am Acad Ophthalmol Otolaryngol. May-Jun. 1969;73(3):482-493.

Doillon et al., "A collagen-based scaffold for a tissue engineered human cornea: physical and physiological properties," Int J Artif Organs. Aug. 2003;26(8):764-773.

Dravida et al., "A biomimetic scaffold for culturing limbal stem cells: a promising alternative for clinical transplantation," J Tissue Eng Regen Med. Jul. 2008;2(5):263-271.

Duan etal, "Biofunctionalization of collagen for improved biological response: scaffolds for corneal tissue engineering," Biomaterials. Jan. 2007;28(1): 78-88.

Engel et al., "Repair of a Traumatic Scleral Rupture With Scleral Imbrication and BioGlue," Retina. Apr.-May 2007;27(4):505-8.

Evans et al. "Epithelialization of a Synthetic Polymer in the Feline Cornea: a Preliminary Study," Invest. Ophthalmol. Vis. Sci. 2000, 41(7):1674-1680.

Evans et al., "A review of the development of a synthetic corneal onlay for refractive correction," Biomaterials. Dec. 2001;22(24):3319-3328.

Evans et al., "Progress in the development of a synthetic corneal onlay," Invest. Ophthalmol. Vis. Sci. 2002; 43(10): 3196-3201.

Griffith et al., "Artificial human corneas: Scaffolds for transplantation and host regeneration" Cornea. Oct. 2002;21(7 Suppl): S54-61.

Griffith et al., "Functional Human Corneal Equivalents Constructed from Cell Lines," Science Dec. 10, 1999, 286(5447):2169-2172.

Gutowska et al., "Thermosensitive Interpenetrating Polymer Networks: Synthesis. Characterization, and Macromolecular Release" Macromolecules 1994; 27(15):4167-4175.

Han et al., "A fibrin-based bioengineered ocular surface with human corneal epithelial stem cells", Cornea, 2002; 21(5):505-510.

Hicks et al., "Keratoprostheses: Advancing Toward a True Artificial Cornea" Surv Ophthalmol. Sep.-Oct. 1997;42(2):175-189.

Homolka et al., "Laser shaping of corneal transplants in vitro: area ablation with small overlapping laser spots produced by a pulsed scanning laser beam using an optimizing ablation algorithm," Phys. Med. Biol. 1999, 44:1169-1180.

Ibrahim-Elzembely, "Human fibrin tissue glue for corneal lamellar adhesion in rabbits: a preliminary study.," Cornea. Nov. 2003;22(8):735-739.

Jeong et al., "Thermosensitive sol-gel reversible hydrogels" Adv Drug Deliv Rev. Jan. 17, 2002;54(1):37-51.

Jones et al., "Silicone Hydrogel Contact Lens Materials Update—Part 1", downloaded from the Internet: <<http://www.siliconehydrogels.com/editorials/index_july.asp>>, Jul. 2004, 4 pages total.

Jones et al., "Silicone Hydrogel Contact Lens Materials Update—Part 2", downloaded from the Internet: <<http://www.siliconehydrogels.com/editorials/index_august.asp>>, Aug. 2004, 4 pages total.

Kaminski et al., "Ten-year follow-up of epikeratophakia for the correction of high myopia," Ophthalmology. Nov. 2003;110(11):2147-2152.

Kaufman et al., "Human fibrin tissue adhesive for sutureless lamellar keratoplasty and scleral patch adhesion a pilot study," Ophthalmology, 110(11): 2168-2172, Nov. 2003.

Khadem et al., "Healing of perforating rat corneal incisions closed with photodynamic laser-activated tissue glue," Lasers in surgery and medicine 2004;35(4):304-311.

Klenkler et al., "EGF-grafted PDMS surfaces in artificial cornea," Biomaterials. Dec. 2005;26(35):7286-96.

Lagali et al., "Innervation of tissue-engineered corneal implants in a porcine model: a 1-year in vivo confocal microscopy study," Invest Ophthalmol Vis Sci. Aug. 2007;48(8): 3537-3544.

Lagali et al., "Innervation of tissue-engineered recombinant human collagen-based corneal substitutes: a comparative in vivo confocal microscopy study," Invest Ophthalmol Vis Sci. Sep. 2008;49(9): 3895-902.

Latkany et al., "Plasma surface modification of artificial corneas for optimal epithelialization," J. Biomed Mater Res 1997; 36(1):29-37.

Lekskul et al., "CxGELSIX: a novel preparation of type VI collagen with possible use as a biomaterial," rnea. Mar. 2000;19(2):194-203.

Li et al., "Cellular and nerve regeneration within a biosynthetic extracellular matrix for corneal transplantation," Proc Natl Acad Sci U S A. Dec. 23, 2003;100(26): 15346-15351.

Li et al., "Recruitment of multiple cell lines by collagen-synthetic copolymer matrices in corneal regeneration," Biomaterials. Jun. 2005;26(16):3093-3104.

Liu et al., "A simple, cross-linked collagen tissue substitute for corneal implantation," Invest Ophthalmol Vis Sci. May 2006;47(5): 1869-1875.

Liu et al., "Alginate microsphere-collagen composite hydrogel for ocular drug delivery and implantation," J Mater Sci Mater Med. Nov. 2008;19(11): 3365-3371.

Liu et al., "Immunological responses in mice to full-thickness corneal grafts engineered from porcine collagen," Biomaterials Sep. 2007;28(26): 3807-3814.

Liu et al., "Properties of porcine and recombinant human collagen matrices for optically clear tissue engineering applications," Biomacromolecules. Jun. 2006;7(6):1819-1828.

Liu et al., "Recombinant human collagen for tissue engineered corneal substitutes," Biomaterials. Mar. 2008;29(9): 1147-1158.

Lynn et al., Degradable poly(β-amino esters): synthesis, characterization, and self-assembly with plasmid DNA, J. Am. Chem. Soc c., 2000; 122(44):10761-10768.

Matteini et al., "Microscopic characterization of collagen modifications induced by low-temperature diode-laser welding of corneal tissue," Lasers in surgery and medicine 2007;39(7):597-604.

Maury et al., "In-vitro development of corneal epithelial cells on a new hydrogel for epikeratoplasty," J Mater Sci Mater Med. Sep. 1997;8(9):571-576.

McDonald, "The future direction of refractive surgery," J Refract Surg 1988; 4(5):158-168.

McLaughlin et al., "Regeneration of corneal cells and nerves in an implanted collagen corneal substitute," Cornea. Jun. 2008;27(5): 580-589.

Menabuoni et al., "Laser-assisted corneal welding in cataract surgery: Retrospective study," J Cataract Refract Surg. Sep. 2007;33(9):1608-1612.

Merrett et al., "Tissue-engineered recombinant human collagen-based corneal substitutes for implantation: performance of type I versus type III collagen," Invest Ophthalmol Vis Sci. Sep. 2008;49(9): 3887-3894.

Moore et al., "Fate of lyophilized xenogeneic corneal lenticules in intrastromal implantation and epikeratophakia," Invest Ophthalmol Vis Sci. Mar. 1987;28(3):555-559.

Nakamura, "Histopathological and immunohistochemical studies of lenticules after epikeratoplasty for keratoconus," British Journal of Ophthalmology 2005;89:841-846.

Ophthalmology Times, "New LASIK device: CIBA Vision to market subepithelial separator", Aug. 1, 2002, 1 page only.

Rafat et al., "PEG-stabilized carbodiimide crosslinked collagen-chitosan hydrogels for corneal tissue engineering," Biomaterials. Oct. 2008;29(29): 3960-3972.

Rafat et al., "Surface modification of collagen-based artificial cornea for reduced endothelialization" J Biomed Mater Res A. Mar. 20, 2008. [Epub ahead of print].

Richards et al., "The relation of the corneal surface to the permanence of glued-on contact lenses," Can J Ophthalmol. Apr. 1971;6(2):98-103.

Ruben "Adhesive keratoprostheses," Trans Ophthalmol Soc U K. 1970;90:551-564.

Schmitz, 'Excimer laser "corneal shaping": a new technique for customized trephination in penetrating keratoplasty,' Graefe's Archive for Clinical and Experimental Ophthalmology, May 2003; 241:423-431.

Shimmura et al. "Biocompatibility of Collagen-based Blended Biomaterials" Invest Ophthalmol Vis Sci 2002;43: E-Abstract 2997. © 2002 ARVO.

Shimmura et al., "Collagen-poly(N-isopropylacrylamide)-based membranes for corneal stroma scaffolds.," Cornea. Oct. 2003;22(7 Suppl): S81-88.

Stenzel et al., "Collagen as a biomaterial," Annu. Rev. Biophys. Bioeng. 1974; 3:231-253.

Stile et al., "Poly(N-isopropylacrylamide)-Based Semi-interpenetrating Polymer Networks for Tissue Engineering Applications. 1. Effects of Linear Poly(acrylic acid) Chains oil Phase Behavior" Biomacromolecules, 2002; 3:591-600.

Stile et al., "Synthesis and Characterization of Injectable Poly(N-isopropylacrylamide)-Based Hydrogels That Support Tissue Formation in Vitro" Macromolecules, 1999; 32:7370-7399.

Stile et al., "Thermo-Responsive Peptide-Modified Hydrogels for Tissue Regeneration" Biomacromolecules 2001; 2(1): 185-194.

Suuronen et al., "Functional innervation in tissue engineered models for in vitro study and testing purposes," Toxicol Sci. Dec. 2004;82(2):525-533.

Suuronen et al., "Innervated human corneal equivalents as in vitro models for nerve-target cell interactions," The FASEB Journal. 2004;18:170-172.

Suuronen et al., "Tissue-engineered injectable collagen-based matrices for improved cell delivery and vascularization of ischemic tissue using CD133+ progenitors expanded from the peripheral blood," Circulation. Jul. 4, 2006;114(1 Suppl):I138-44.

Sweeney et al., "A synthetic polymer as a corneal onlay ," [ARVO Abstract] Invest Ophthalmol Vis Sci 40(4),S638 Abstract nr 3361, Jul. 2001.

Trinkaus-Randall et al. "Biological response to a synthetic cornea" J. Controlled Release 1998; 53(1-3):205-214.

Trinkaus-Randall et al. "Implementation of a synthetic cornea: design, development and biological response," Artif Organs. Nov. 1997;21(11):1185-1191.

Tsai et al., "Reconstruction of damaged corneas by transplantation of autologous limbal epithelial cells", The New England Journal of Medicine Jul. 2000, 343(2):86-93.

Vascotto et al., "Localization of candidate stem and progenitor cell markers within the human cornea, limbus, and bulbar conjunctiva in vivo and in cell culture," Anat Rec A Discov Mol Cell Evol Biol. Aug. 2006;288(8):921-931.

Vernon et al., "Thermally reversible polymer gels for biohybrid artificial pancreas" Macromol. Symp. 1996;109:155-167.

Vinciguerra et al., "Butterfly laser epithelial keratomileusis for myopia," Journal of refractive surgery 2002;18(3 Suppl):S371-3.

Yoshida et al., "Comb-type grafted hydrogels with rapid deswelling response to temperature changes" Nature, Mar. 16, 2002; 374:240-242.

U.S. Appl. No. 60/715,411, filed Sep. 9, 2005.

US 6,773,442, 08/2004, Pallikaris et al. (withdrawn)

* cited by examiner

FIG. 1

CORNEAL ONLAYS AND WAVEFRONT ABERRATION CORRECTION TO ENHANCE VISION

CROSS-REFERENCE TO RELATED APPLICATIONS

This application is a continuation of U.S. application Ser. No. 11/128,824, filed May 13, 2005, which application claims the benefit of U.S. Provisional Application Ser. No. 60/573,657, filed May 20, 2004, the disclosure of each of which is hereby incorporated in its entirety herein by this reference.

BACKGROUND OF THE INVENTION

Field of the Invention

The present invention relates to devices and methods of enhancing the vision of an individual. In particular, the invention relates to enhancing vision of an individual by measuring one or more wavefront aberrations of the individual, and shaping an ocular implant element into a corneal onlay that is configured to correct for the wavefront aberration or aberrations.

SUMMARY OF THE INVENTION

The present invention relates to the use of corneal onlays and wavefront technology to enhance an individual's (e.g., a person or animal) vision, and to processes for making such onlays. Some methods involve measuring one or more wavefront aberrations of an individual, and altering an ocular implant element or the individual's eye based on the wavefront aberrations.

In one embodiment, a method for enhancing vision of an individual comprises: providing an ocular implant element, such as a lens or a blank; measuring a wavefront aberration of an eye of an individual; and altering the ocular implant element based on the measured wavefront aberration to provide a correction for the wavefront aberration when the altered ocular implant element is located in an eye of the individual between the epithelial cell layer and the Bowman's membrane. The ocular implant element may be altered by ablating one or more portions of the element to form a corneal onlay effective in correcting the wavefront aberrations.

In another embodiment, a method for enhancing vision of an individual comprises molding a corneal onlay having an ocular power effective in correcting the vision of an eye of an individual; measuring a wavefront aberration of the eye of the individual; and ablating a portion of the onlay to correct the measured wavefront aberration.

In another embodiment, a method for enhancing vision of an individual comprises molding a corneal onlay having an ocular power effective in correcting the vision of an eye of an individual; measuring a wavefront aberration of the eye of the individual; and ablating a portion of the eye of the individual to correct the measured wavefront aberration.

The foregoing methods may also comprise a step of placing the altered ocular implant element or the corneal onlay in the eye between the epithelial cell layer and the Bowman's membrane. The methods may also comprise forming an epithelial flap or forming an epithelial pocket before placing the altered ocular implant element or corneal onlay in the eye. The methods may also comprise placing the epithelial flap over the altered ocular implant element or corneal onlay positioned substantially on the Bowman's membrane.

In another embodiment, a method of producing a corneal onlay, comprises measuring a wavefront aberration of an eye of an individual; and altering an ocular blank without a corrective ocular power or a lens having an ocular power to provide a correction for the wavefront aberration of the eye of the individual when the altered ocular blank or altered lens is located between the epithelial cell layer and the Bowman's membrane.

In another embodiment, a method of producing a corneal onlay, comprises altering an ocular blank without a corrective ocular power or a lens having a fixed optical power to provide a correction for a wavefront aberration of an eye of an individual when the altered ocular blank or lens is located between an epithelial cell layer and Bowman's membrane of the individual.

The methods may also comprise molding the ocular blank or lens from an ophthalmically acceptable material. The altering step may comprise ablating one or more portions of the blank or lens. For example, the methods may comprise using a lathe to alter the blank or the lens to form the corneal onlay. The lathe may be used directly on the blank or lens, or the lathe may be used on an insert, such as metal insert, that makes or is used in making a corneal onlay mold, such as a thermoplastic mold.

Any feature or combination of features described herein are included within the scope of the present invention provided that the features included in any such combination are not mutually inconsistent as will be apparent from the context, this specification, and the knowledge of one of ordinary skill in the art. In addition, any feature or combination of features may be specifically excluded from any embodiment of the present invention.

Additional advantages and aspects of the present invention are apparent in the following detailed description.

DETAILED DESCRIPTION

A typical human eye has a lens and an iris. The posterior chamber is located posterior to iris and the anterior chamber is located anterior to iris. The eye has a cornea that consists of five layers, as discussed herein. One of the layers, the corneal epithelium, lines the anterior exterior surface of cornea. The corneal epithelium is a stratified squamous epithelium that extends laterally to the limbus.

The five layers of the cornea include the corneal epithelium, the Bowman's membrane, the stroma, Descemet's membrane, and the endothelium. The corneal epithelium usually is about 5-6 cell layers thick (approximately 50 micrometers thick), and generally regenerates when the cornea is injured. The corneal epithelium provides a relatively smooth refractive surface and helps prevent infection of the eye. The Bowman's membrane lies between the epithelium and the stroma and is believed to protect the cornea from injury. The corneal stroma is a laminated structure of collagen which contains cells, such as fibroblasts and keratocytes, dispersed therein. The stroma constitutes about 90% of the corneal thickness. The corneal endothelium typically is a monolayer of low cuboidal or squamous cells that dehydrates the cornea by removing water from the cornea. An adult human cornea is typically about 500 µm (0.5 mm) thick and is typically devoid of blood vessels.

The present invention relates to the use of corneal onlays to enhance or improve vision in an individual, such as a person or an animal. A corneal onlay is a lens with a vision-correcting or vision-enhancing optical power and that is configured, such as sized and shaped, to be placed between the epithelium and the Bowman's membrane of an eye of an individual. Corneal onlays include a major portion that is located between the epithelium and Bowman's membrane. In some situations, a minor portion of the onlay may penetrate Bowman's membrane and/or the underlying stroma. In comparison, corneal inlays are configured to be placed in the cornea, such as in the stroma of the cornea. In other words, corneal inlays include a major portion that is placed in the corneal stroma. Contact lenses are configured to be placed on the epithelium of an eye.

Figure 1:
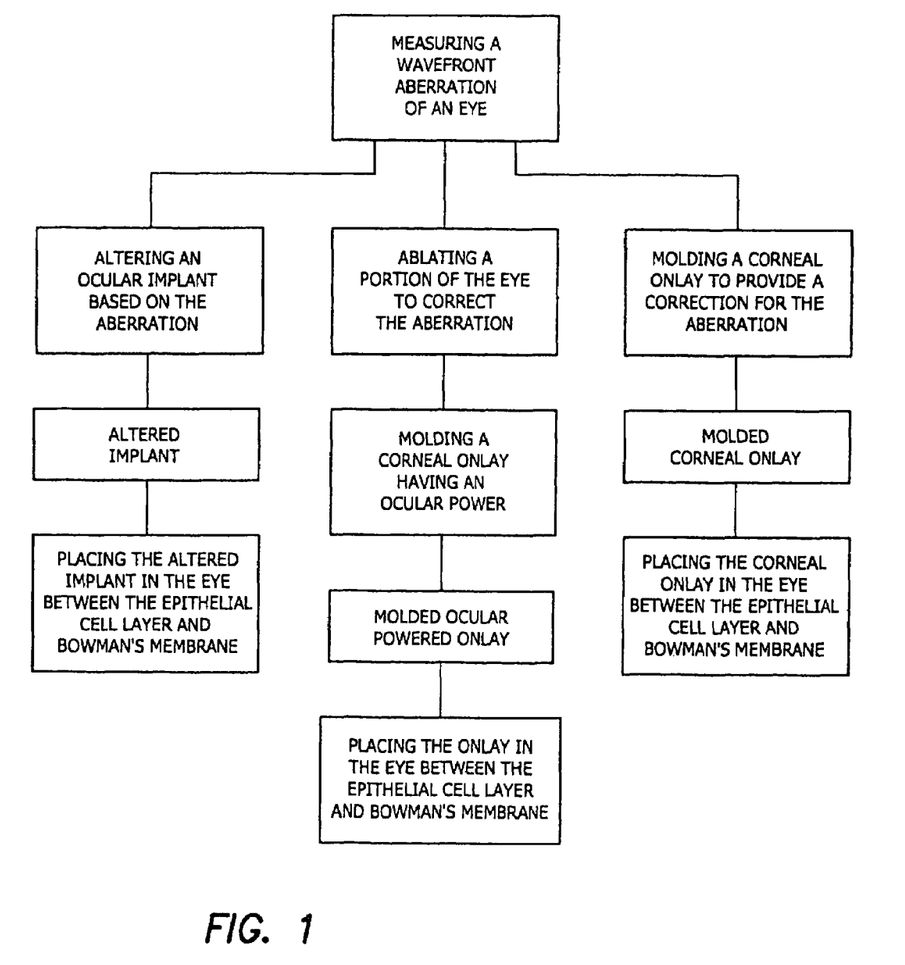
FIG. 1 is a block diagram illustrating a number of different embodiments of the present invention.

In one aspect of the present invention, methods for enhancing vision are disclosed which utilize a corneal onlay and wavefront aberration measurements. In another aspect of the present invention, method for producing or manufacturing corneal onlays are disclosed. To facilitate understanding of the present invention, FIG. 1 is provided and illustrates one or more alternate embodiments of such methods for enhancing vision and methods for producing or manufacturing corneal onlays.

One embodiment of the present methods of enhancing vision comprises the steps of providing an ocular implant element, measuring one or more wavefront aberrations of an eye of an individual, and altering the ocular implant element based on the measured wavefront aberration or aberrations to provide correction for the wavefront aberration or aberrations when the altered ocular implant element is located between the epithelial cell layer or epithelium and the Bowman's membrane. The altered ocular implant element may be understood to be a corneal onlay effective in correcting or enhancing an individual's vision when the element is placed between the epithelium and the Bowman's membrane.

The ocular implant element may be a blank, such as an element without a substantial optical power, or an element with an optical power of about 0 diopters. Or the ocular implant element may be a lens, or in other words, an element with a desired or pre-determined optical power, such as a vision correcting optical power. The optical power of the lens may be determined for a specific individual, or for a group of individuals.

The ocular implant element may be provided in a package of a plurality of elements, or it may be provided in a package by itself. The ocular implant element may be sterile or non-sterile. Typically, the ocular implant element is provided by a manufacturer of ophthalmic blanks or vision correcting lenses. The ocular implant elements may be mass produced or may be produced and provided based on an individual's needs and desires. In other words, the ocular implant elements may be generically produced, such as for ocular implant elements that do not have an optical power, or for ocular implant elements that have a pre-determined or fixed optical power. Or, the ocular implant elements may be customized in their production to suit one or more individuals.

The ocular implant element comprises an ophthalmically acceptable material. For example, the ocular implant element may be produced from a material that is optically clear or otherwise does not negatively affect or reduce an individual's vision when the implant element is located on an eye of the individual. In addition, the material from which the implant element is produced provides for sufficient gas and nutrient exchange between the Bowman's membrane and epithelium to maintain a viable, fully functioning epithelium.

The material from which the ocular implant element is produced may comprise a polymeric component comprising one or more polymers. The polymers of the polymeric component may be synthetic or naturally occurring, or both. Elements that comprise a plurality of polymers may be formed by cross-linked polymers or non-crosslinked but physically interwoven polymers.

In certain embodiments, the ocular implant element may be made from collagen, such as purified collagen. The collagen may be collagen Type I, which is the type of collagen that defines the bulk of the corneal stroma, or the collagen may be non-Type I collagen. Or the implant element may be made from combinations of different types of collagen, such as types III, IV, V, and VII. The collagen may be obtained from an animal source, for example, the collagen may be human collagen, bovine collagen, porcine collagen, avian collagen, murine collagen, equine collagen, among others. Many different types of collagen useful in the lenses of the present invention are publicly available from companies, such as Becton Dickenson. Or, the collagen may be recombinantly synthesized, such as by using recombinant DNA technology. One source of publicly available recombinant collagen is FibroGen, South San Francisco, Calif. Alternatively, or in addition, recombinant collagen may be prepared and obtained using the methods disclosed in PCT Publication No. WO 93/07889 or WO 94/16570. In addition, the ocular implant element may be made from materials described in one or more of the following: WO 2004/015090, WO 2004/014969, and WO 99/37752.

In addition, or alternatively, the ocular implant element may be made from a polymeric hydrogel, as understood by persons of ordinary skill in the art. A polymeric hydrogel includes a hydrogel-forming polymer, such as a water swellable polymer. The hydrogel itself includes such a polymer swollen with water. Polymeric hydrogels useful in the present corneal onlays typically have about 30% to about 80% by weight water, but may have about 20% to about 90% by weight water, or about 5% to about 95% by weight water, and have refractive indices between about 1.3 and about 1.5, for example about 1.4, which is similar to the refractive indices of water and a human cornea.

Examples of suitable hydrogel-forming polymer materials or components of the disclosed ocular implant elements include, without limitation, poly(2-hydroxyethyl methacrylate) PHEMA, poly(glycerol methacrylate) PGMA, polyelectrolyte materials, polyethylene oxide, polyvinyl alcohol, polydioxaline, poly(acrylic acid), poly(acrylamide), poly(N-vinyl pyrilidone) and the like and mixtures thereof. Many of such materials are publicly available. In addition, one or more monomers which do not themselves produce homopolymers which are not hydrogel-forming polymers, such as methylmethacrylate (MMA), other methacrylates, acrylates and the like and mixtures thereof, can also be included in such hydrogel-forming polymer materials provided that the presence of units from such monomers does not interfere with the desired formation of a polymeric hydrogel.

Alternatively, the ocular implant elements may be manufactured from a biocompatible, non-hydrogel material or component, such as disclosed in U.S. Pat. No. 5,713,957. Examples of non-hydrogel materials include, and are not limited to, acrylics, polyolefins, fluoropolymers, silicones, styrenics, vinyls, polyesters, polyurethanes, polycarbonates, cellulosics, or proteins including collagen based materials. In addition, the ocular implant element or the corneal onlay may comprise a cell growth substrate polymer, such as those disclosed in U.S. Pat. No. 5,994,133.

Thus, the ocular implant elements may comprise a synthetic material, a non-synthetic material, or a combination thereof. In one embodiment, the ocular implant element is made entirely from a synthetic material. In certain embodiments, the ocular implant element is made from a combination of collagen and a synthetic material, including, combinations of bovine collagen and a synthetic material, and combinations of recombinant collagen and synthetic materials. In additional embodiments, the lens may include a poly (N-isopropylacrylamide) (polynipaam) component.

In reference to the disclosure herein, a corneal onlay refers to a vision correcting lens that is suitable for placement on an individual's eye to provide enhancements to the individual's vision. The present corneal onlays may be produced by altering a blank or a lens based on one or more wavefront aberrations of an individual's eye or eyes, as described below.

The methods of enhancing vision may also comprise measuring one or more wavefront aberrations of an eye of an individual. The refractive error or errors in an eye may be measured using wavefront technology, as is known to persons of ordinary skill in the art. For example, a description of wavefront technology and the measurements of wavefront aberrations is provided in U.S. Pat. No. 6,086,204 (Magnate) and WO 2004/028356 (Altmann).

A wavefront aberration is the three dimensional profile of the distance between a real light wave front of a central spot of light and a reference surface, e.g., an ideal spherical shape, as shown in FIG. 1 of U.S. Pat. No. 6,585,375, and as described in Mierdel et al., "Der Ophthalmologe", No. 6, 1997. A wavefront aberration may be understood to be an optical path difference between an actual image wavefront and an ideal reference wavefront centered at an image point, at any point in the pupil of an eye. Methods of measuring wave-front aberration are well known to persons of ordinary skill in the art.

Briefly, and as described by Nader, N., *Ocular Surgery News*, "Learning a new language: understanding the terminology of wavefront-guided ablation" (Feb. 1, 2003), an aberrometer (e.g., an instrument that measures the aberrations of an eye) may be used to measure an aberrated image that leaves an eye, or may be used to measure the shape of a grid projected onto the retina. For example, while a patient is maintaining a view on a visual fixation target, a relatively narrow input laser beam may be directed through the pupil and focused onto the retina of the patient's eye to generate a point-light source on the retina. The light is reflected from the retina back through the pupil, and the wavefront of the light passing from the eye is passed to a wavefront sensor. As understood by persons of ordinary skill in the art, a wavefront can be defined as a surface that connects all field points of an electromagnetic wave that are equidistant from a light source. The light rays leave the eye and may pass through an array of lenses that detects the light rays' deviation. The wavefront gets deviated or distorted by inhomogeneities in the refractive properties in the refractive media of the eye, such as the lens, the cornea, the aqueous humor, and the vitreous humor. The resulting image is then typically recorded by a charge coupled device (CCD) camera, for example.

The wavefront is then typically reconstructed and the deviations are described mathematically in three dimensions. The wavefront deviations may be calculated, at least in part, by analyzing the direction of the light rays. Generally, parallel light beams indicate a wavefront with little, if any, aberrations, and nonparallel light beams indicate a wavefront with aberrations that do not give equidistant focal points.

Typically, Zernike polynomials are used to measure or analyze the ocular aberrations. Each Zernike polynomial describes a shape or a three-dimensional surface. As understood by persons of ordinary skill in the art, Zernike polynomials are an infinite set, but in ophthalmology, the Zernike polynomials are usually limited to the first fifteen polynomials. Second-order Zernike terms represent conventional aberrations, such as defocus and astigmatism. Aberrations above second-order aberrations are called higher-order aberrations. Higher-order aberrations typically cannot be corrected by conventional spherocylindrical lenses. Examples of higher-order aberrations include, but are not limited to, coma, spherical aberrations, trefoil (wavefronts with threefold symmetry), and quadrefoil (wavefront shapes with fourfold symmetry). Many higher-order aberrations are not symmetrical, but some higher-order aberrations, such as spherical aberrations, may be symmetrical.

The refractive error measurements may be transmitted to a lens-shaping machine or device, such as a computerized lathe, where the shape of the ocular implant element is determined using the information from the wavefront device. Other lathes may also be used, such as non-computerized lathes. Other devices may include one or more lasers that can be used to shape the ocular implant element or a tool used to manufacture an ocular implant element. A lathe may be used to alter the shape of the ocular implant element by ablating one or more portions of the lens (e.g., the lathe acts or is used directly on the ocular implant element), or by altering the shape of an insert, such as a metal insert, that is used to make a mold for a lens, such as a thermoplastic mold. Such inserts are similar to inserts used in the manufacture of contact lenses, as understood by persons of ordinary skill in the art. The shaped ocular implant element that has been designed based on the wavefront aberrations may be understood to be a corneal onlay.

In accordance with the present invention, the wavefront aberration of an individual's eye may be measured and analyzed to facilitate appropriate corneal onlay construction. The ocular implant element (e.g., the blank or the lens) can then be shaped, as discussed herein, taking into account any measured wavefront aberrations. Thus, a corneal onlay is obtained with a lens body configured to correct a wavefront aberration of a person's eye. The wavefront aberration corrective surface may be provided on either the anterior surface, the posterior surface, or both the anterior and posterior surfaces. Thus, in certain embodiments, the present onlays correct or reduce higher-order wavefront aberrations. In situations where the higher-order wavefront aberrations are asymmetrical, the lenses are configured to substantially maintain a desired orientation to correct the wavefront aberrations.

After measuring the wavefront aberration or aberrations of a person's eye, a method of enhancing vision of an individual comprises altering the ocular implant element based on the measured wavefront aberration. The altering is effective in providing a correction for the wavefront aberration or aberrations when the ocular implant element is located on an eye between the epithelial cell layer and the Bowman's membrane.

As discussed herein, the altering step may comprise ablating one or more portions of the ocular implant element. For example, one or more portions of the ocular implant element may be ablated or otherwise removed using a lathe, such as a computerized lathe, a laser, or any other suitable lens-shaping device.

When the ocular implant element has no corrective ocular power (e.g., a blank), or has a corrective ocular power (e.g., a lens), ablation of at least a portion of the element is effective to provide a correction for the wavefront aberration or aberrations. The ablation may be effective to provide a spherical power.

The method of enhancing vision described above may also comprise a step of placing the altered ocular implant element (or corneal onlay) in the eye of the individual between the epithelial cell layer, such as the epithelium, and the Bowman's membrane. The corneal onlay may be placed in the eye by first forming an epithelial flap on the individual's eye, and then placing the corneal onlay on the exposed Bowman's membrane. This method may also comprise an additional step of placing the epithelial flap over the corneal onlay when the onlay is positioned on the Bowman's membrane. Or, the onlay may be placed in a pocket formed between the epithelium or epithelial cell layer and the Bowman's membrane. The corneal onlay may thus be positioned entirely between the epithelium and Bowman's membrane.

The epithelial flap may be formed by removing a portion of the epithelium using a separator that can separate the epithelium from Bowman's membrane. One example of a separator is a sub-epithelial separator developed by Dr. Ioannis Pallikaris (Greece), such as the separator disclosed in U.S. Patent Publication Nos. 2003/0018347 and 2003/0018348. The separator may include a suction device, or ring, that can deliver suction to the epithelium to cause the epithelium to be lifted from the cornea. A cutting device, such as a blade, including a microkeratome, which may or may not be a part of the separator can then be used to cut the portion of the epithelium that is being lifted from the cornea to create a flap, or to completely remove that portion of the epithelium that is being manipulated.

Or the cutting device may use electromagnetic energy to cut the epithelium. When electromagnetic energy is used as the epithelial cutting device, it may be desirable to use an electromagnetic energy source, such as a laser, with reduced, and preferably no, thermal energy to help reduce cellular injury during the procedure. For example, a fluid, such as water or saline, may be used in conjunction with the electromagnetic energy to reduce thermal damage caused by the electromagnetic energy. When removing the corneal epithelium, it may be desirable to remove one or more small portions of Bowman's membrane, as indicated herein to facilitate more rapid healing of the ocular tissue. However, in certain situations, the Bowman's membrane is left entirely intact.

An epithelial pocket may be formed by making an incision in the epithelium. An incision may be formed at any desired region around the epithelium, but in preferred embodiments, the incision or incisions is formed either in the temporal portion of the epithelium (e.g., the portion of the epithelium that is located away from the nose of a patient), or in the medial portion of the epithelium. The incision is preferably formed to provide an opening in the epithelium, for example, of suitable size, to accommodate a corneal onlay to be inserted therethrough without creating an epithelial flap. Typically, the incision will be formed away from the pupil.

The incision can be made by cutting or slicing the epithelium using a sharp instrument, such as a microkeratome and the like, including the microkeratome disclosed hereinabove. Alternatively, or in addition, the incision can be made by using blunt dissection to separate epithelial cells to create an opening in the epithelium without cutting or slicing the epithelium. Blunt dissection provides an advantage of reduced injury to the epithelial cells and/or epithelial tissue.

The onlay may then be inserted through the incision. The onlay may be inserted by using forceps, or other similar device. Or, the onlay may be inserted by using an inserter that is configured to deform at least a portion of the onlay so that the onlay can fit through the incision, for example, through a smaller incision that would be necessary if the onlay was not deformed. For example, the onlay may be folded or rolled or curled so that its cross-sectional area is reduced while it is being inserted beneath the epithelium. A corneal onlay insertion device may be a syringe like device which includes a body with a distal end dimensioned to pass the lens under the corneal epithelium of an eye. In certain situations, the corneal onlay insertion device may be similar, or at least somewhat similar, to well known and publicly available intraocular lens inserters.

The epithelium may be raised prior to cutting the epithelium. The epithelium may be raised using any suitable technique that permits the epithelium to be separated from Bowman's membrane preferably without substantially damaging Bowman's membrane or the corneal stroma. In certain embodiments, a portion of the epithelium is raised using a vacuum. The vacuum may be provided with a microkeratome, such as with the separator disclosed in U.S. Patent Publication Nos. 2003/0018347 and 2003/0018348, or it may be provided as a separate instrument.

Alternatively, or in addition, the epithelium may be lifted by delivering a fluid beneath a portion of the epithelium. The delivery of fluid causes the epithelium to swell to create a bulge of epithelial tissue that is spaced apart from Bowman's membrane, as indicated above. One suitable fluid may include sodium chloride, for example, an aqueous sodium chloride solution. Another fluid may include a gel. The gel may be a gel that includes at least one water soluble or water swellable polymeric material, for example, at least one cellulosic component, such as hydroxymethylcellulose and the like, and/or one or more other water soluble or water swellable polymeric materials. In one specific embodiment, the fluid comprises a gel sold as GENTEAL gel by CibaVision, Duluth, Ga.

The present corneal onlays may also be inserted between an epithelium and Bowman's membrane in a method comprising a single step of forming an epithelial pocket and inserting the onlay at the same time. For example, the onlay may be located on an epithelial delaminator blade during a cutting procedure. After the pocket has been formed, the onlay can be removed from the delaminator blade and retained in the epithelial pocket as the delaminator blade is removed from the pocket.

In another embodiment of the present invention, a method for enhancing vision of an individual comprises molding an ocular implant element to have an ocular power effective in correcting the vision of an eye of a person, measuring the wavefront aberration of the eye of the individual, and ablating a portion of the individual's eye on which the molded ocular implant element is to be placed to correct the measured wavefront aberration or aberrations.

The foregoing method may also comprise a step of placing the molded ocular implant element (e.g., corneal onlay) in the eye between the epithelial cell layer and the Bowman's membrane, as described herein. For example, the corneal onlay may be placed under an epithelial flap, or it may be placed in an epithelial pocket.

In another aspect of the present invention, a method of producing a corneal onlay comprises measuring a wavefront aberration or aberrations of an eye of an individual, and altering a blank (e.g., an ocular implant element without an optical power) to provide a correction for the wavefront aberration or aberrations of the eye when the altered blank (e.g., corneal onlay) is located between the epithelial cell layer and the Bowman's membrane.

Or, a method may comprise altering a blank or a lens based on a wavefront aberration of an eye or eyes of an individual to provide a correction for the wavefront aberration. Such a method does not necessarily require a step of measuring a wavefront aberration or aberrations of the eye. But, the method may comprise a step of receiving information regarding the wavefront aberration or aberrations of an eye or eyes of an individual. The information could include results from a wavefront aberration measurement procedure performed by a physician. The information could be provided as printed results, or may be transmitted electronically to an onlay manufacturer, which can then alter the blank or lens to correct for the wavefront aberrations. For example, a physician could measure wavefront aberrations of an eye of an individual, and then transmit that information regarding the wavefront aberrations, such as the type of aberrations or the location of the aberrations, to an onlay manufacturer. The onlay manufactured can then produce onlays that can provide the desired vision correction taking into account the wavefront aberrations, in accordance with the present invention.

The foregoing method may also comprise a step of molding the blank from an ophthalmically acceptable material, as described herein. The molding can be performed using any conventional molding process similar or identical to the molding of contact lenses, as understood by persons of ordinary skill in the art. As discussed herein, the altering step may comprise ablating at least a portion of the blank, which may be effective to provide a spherical power. For example, the ablating can be accomplished utilizing a lathe, a laser, or any lens altering machine or device, or combination of devices.

When lasers are used, the laser can be delivered towards an ablation zone or area of the blank or lens as a uniform number of pulses, or in a pattern where the pulse density varies over the ablation zone. One example of a suitable laser is the Star S4 excimer laser available from VISX.

The ablation of the blank or lens by a laser, lathe, or other similar device, is effective in providing a desired curvature, as discussed herein. The amount of the blank or lens material removed can vary across the ablation zone, for example, more material can be removed from a central portion relative to peripheral portions. Or, more material may be removed from peripheral portions relative to a central portion.

In another embodiment, a method of producing a corneal onlay comprises measuring one or more wavefront aberrations of an individual's eye or eyes, and altering at least a portion of a lens (e.g., an ocular implant element having an optical power) to provide a correction for the wavefront aberration or aberrations when the altered lens (e.g., corneal onlay) is placed between the epithelial cell layer and the Bowman's membrane.

The foregoing method may also comprise a step of molding an ophthalmically acceptable material into the lens. Similar to the methods above, the altering step may comprise ablating at least a portion of the lens, for example, ablating at least a portion of the lens to have a spherical power.

In view of the above, corneal onlays are disclosed that are produced by any of the methods above. The present corneal onlays and methods thus provide permanent yet reversible, if necessary, vision enhancement.

The present corneal onlay has an anterior surface, a posterior surface, a peripheral edge disposed at the juncture of the anterior surface and the posterior surface. The anterior surface is typically convex and the posterior surface is typically concave, however, the posterior surface may also include one or more planar portions or surfaces, or may be substantially planar.

The corneal onlay may also include an optic zone and a peripheral zone. Typically, the optic zone is bounded by the peripheral zone, or in other words, the optic zone is generally centrally located about an optical axis, such as a central optical axis, of the lens and the peripheral zone is disposed between an edge of the optic zone and the peripheral edge of the corneal onlay. Additional zones and onlay configurations may be provided with the onlay depending on the particular visual deficiency experienced by the patient.

In addition, the present corneal onlays may have junctionless zones, such as two or more zones that do not have a visually or optically detectable junction. The zones of the onlays may be smooth and continuous, and the onlays may be optically optimized to correct not only refractive errors, but also other optic aberrations of the eye and/or the optical device independently or in combination with correcting refractive errors. As understood by persons skilled in the art, corneal onlays may be structured to correct visual deficiencies including, and not limited to, myopia, hyperopia, astigmatism, and presbyopia. The onlay may enhance or improve visual deficiencies by either optical means or physical means imposed on the stroma of the eye, or a combination thereof. Thus, the corneal onlay may be a monofocal lens or a multifocal lens, including, without limitation, a bifocal lens.

In addition, or alternatively, the corneal onlay may be a toric lens. For example, the onlay may include a toric region which may be effective when placed on an eye with an astigmatism to correct or reduce the effects of the astigmatism. The onlay may include a toric region located on the posterior surface of the onlay, or the onlay may include a toric region located on the anterior surface. A corneal onlay comprising a toric region may be referred to as a toric onlay. The toric onlay does not necessarily require a specific axis since the surgeon can align the onlay to the correct axis of the individual receiving the onlay. The axis is typically used to align a cylinder of the lens to the patient based on the inherent toricity of the individual's eye. Advantageously, toric onlays without an axis, as described above, may provide a reduced number of stock keeping units (SKUs) in manufacturing the onlays. A toric onlay may comprise one or more markings, such as provided on or in the onlay, or on a removable material attached to the onlay, which are effective in showing where the cylinder is on the onlay. Advantageously, toric onlays may be used without requiring a ballast to maintain proper orientation of the onlay on the eye since the onlay may be held in a relatively fixed position by the epithelium of the appliance. However, a ballast may be provided if desired. In certain embodiments, the onlay may include a ballast, such as a prism, or it may include one or more thinned regions, such as one or more inferior and/or superior thin zones. In onlays configured to correct presbyobia, the onlay may include one or more designs, such as concentric, aspheric (either with positive and/or negative spherical aberration), diffractive, and/or multi-zone refractive. One example of suitable corneal onlays is disclosed in U.S. application Ser. No. 10/661,400, filed Sep. 12, 2003.

The corneal onlays disclosed herein may have an optical power ranging from about −10.00 diopters to about +10.00 diopters, although other optical powers may be provided, and such other optical powers are within the scope of the present invention. Typically, corneal onlay will have a diameter between about 5 mm and about 12 mm. Preferably, the diameter of the onlay will be between about 7 mm and about 10 mm. The optic zone of the onlay typically ranges from about 5 to about 11 mm, and preferably ranges from about 6 mm to about 8 mm, in diameter. The optic zone may be provided on either the anterior or posterior surface of the onlay.

The posterior surface of the corneal onlay is specifically configured to substantially align with the anterior surface of a de-epithelialized eye. Thus, the posterior surface of the onlay may include one or more spherical or aspherical dimensions with a base curve that ranges from about 5.0 mm to about 12.0 mm in diameter, preferably from about 6.0 mm to about 9.0 mm, and more preferably about 7.0 mm to about 8.5 mm. The thickness of the lens 40 at or near the center of the lens (i.e., the center thickness) is typically greater than about 10 micrometers and is less than about 300 micrometers. Preferably, the center thickness is between about 30 micrometers and about 200 micrometers. The exact or specific thickness of the central region may be determined on a case-by-case basis by one of ordinary skill in the art since the maximum thickness is optical power and refractive index dependent.

The edge thickness of the corneal onlay is typically, but not always, less than the center thickness of the onlay. The edge thickness should be thin enough to facilitate epithelial cell growth at the juncture of the onlay and the Bowman's membrane or stroma of an eye, and may be thin enough to promote additional epithelial cell migration over the edge of the onlay. Typically, the edge thickness of the onlay is less than about 120 micrometers. In certain embodiments, the onlay has an edge thickness less than about 60 micrometers, and preferably less than about 30 micrometers. In a preferred embodiment, the lens 40 has an edge thickness of about 0 micrometers (for example, the thickness of a sharp knife edge). The onlay edge may be rounded on both the anterior and posterior surfaces. Alternatively, the onlay edge may include a rounded anterior surface and an apex on or near the posterior surface. Or, the onlay edge may be shaped as a knife edge.

In certain embodiments, the corneal onlay may also include a cellular attachment element. The cellular attachment element facilitates the stable positioning of an epithelial layer over the onlay. Although cellular attachment elements may be desirable when utilizing onlays fabricated from collagen, most cellular attachment components may find increased use in the hydrogel or non-hydrogel lenses described hereinabove.

Cellular attachment elements may include physical perturbations of the onlay, such as indentations provided in the anterior surface that facilitate cellular attachment and do not alter the optical properties of the onlay. Indentations included pores that extend through the lens from the anterior surface to the posterior surface of the onlay. The indentations may be provided over the entire onlay or over a fraction of the onlay. The indentations may also be provided in specific patterns and dimensions that facilitate cellular attachment of the epithelial layer to the onlay.

The cellular attachment element may also comprise a polymer that supports adhesion of the epithelial cells to the onlay. As discussed above, the onlay may be made essentially from such polymers as disclosed in U.S. Pat. No. 5,994,133. In addition, these cell growth substrate polymers may be chemically bonded or otherwise coated on the surface of a hydrogel or collagen based onlay to facilitate cellular attachment to the onlay.

The cellular attachment element may also comprise a corneal enhancer molecule, such as a corneal enhancer molecule that specifically binds to a molecule present on the extracellular surface of an epithelial cell. Examples of suitable corneal enhancer molecules include peptides, such as the tripeptide, RGD, the pentapeptide, YIGSR, extracellular matrix proteins, corneal growth factors, and ligand-specific corneal enhancer species, such as laminin, fibronectin, substance P, fibronectin adhesion promoting peptide sequence, FAP, insulin-like growth factor-1 (IGF-1), k-laminin, talin, integrin, kalinin, fibroblast growth factor (FGF), and TGF-$\beta$, as disclosed in U.S. Patent Publication No. US 2002/0007217 A1. These corneal enhancer molecules may include a tether, which may enhance the ability of epithelial cells to attach and migrate over the onlay.

In one example, an ocular implant element may be manufactured by molding a synthetic material, such as collagen, in a lens mold having a desired structure to correct a visual deficiency, thereby forming a lens. The collagen lens may be modified on its surface to promote cellular attachment of the epithelial cells. The collagen lens may then be altered to correct one or more wavefront aberrations measured from an individual's eye or eyes.

While this invention has been described with respect to various specific examples and embodiments, it is to be understood that the invention is not limited thereto and other embodiments are within the scope of the invention.

A number of cited publications, patents, and patent applications have been cited hereinabove. Each of the cited publications, patents, and patent applications are hereby incorporated by reference in their entireties.

What is claimed is:

1. A method for enhancing vision of an individual comprising:

measuring a wavefront aberration of an eye of the individual, the eye comprising an epithelial cell layer and a Bowman's membrane; and altering an ocular implant element based on the measured wavefront aberration to provide a correction for the wavefront aberration, wherein the altered ocular implant element is placed in the eye between the epithelial cell layer and the Bowman's membrane to correct the wavefront aberration and wherein the posterior surface of the ocular implant is configured to substantially align with the Bowman's membrane.

2. The method of claim 1, wherein the ocular implant element is a blank without a corrective ocular power or a lens having an optical power.

3. The method of claim 1, wherein the ocular implant element is a blank without a corrective ocular power or a lens having an optical power, and the step of altering the ocular implant element comprises ablating at least a portion of the blank or lens to provide a correction for the wavefront aberration.

4. The method of claim 3, wherein the step of altering the ocular implant element comprises ablating at least a portion of the blank to provide a spherical power.

5. The method of claim 1, further comprising a step of placing the altered ocular implant element in the eye between the epithelial cell layer and the Bowman's membrane.

6. The method of claim 5, further comprising a step of forming an epithelial flap or epithelial pocket to facilitate placement of the altered ocular implant element in the eye.

7. A method of producing a corneal onlay, comprising:

measuring a wavefront aberration of an eye of an individual, the eye comprising an epithelial cell layer and a Bowman's membrane; and altering at least a portion of a lens having a fixed optical power to provide a correction for the wavefront aberration of the eye of the individual and wherein the altered lens is placed between the epithelial cell layer and the Bowman's membrane to correct the wavefront aberration and wherein the posterior surface of the ocular implant is configured to substantially align with the Bowman's membrane.

8. The method of claim 7, further comprising a step of molding the ocular blank or the lens from an ophthalmically acceptable material.

9. The method of claim 7, wherein altering the ocular blank or the lens comprises ablating at least a portion of the ocular blank or the lens, respectively.

10. The method of claim 7, wherein altering the ocular blank or the lens comprises ablating at least a portion of the blank or the lens to have a spherical power, respectively.

11. A corneal onlay produced by the method of claim 7.

12. A method of producing a corneal onlay, comprising:
altering an ocular blank without a corrective ocular power or at least a portion of a lens having a fixed optical power, to provide a correction for a wavefront aberration of an eye of an individual and wherein the altered ocular blank or lens placed between an epithelial cell layer and Bowman's membrane of the individual to correct the wavefront aberration and wherein the posterior surface of the ocular implant is configured to substantially align with the Bowman's membrane.

13. The method of claim 12, further comprising a step of:
receiving information regarding a wavefront aberration measured for the eye of the individual.

14. The method of claim 12, further comprising a step of molding the ocular blank or lens from an ophthalmically acceptable material.

15. The method of claim 12, wherein altering the ocular blank or lens comprises ablating at least a portion of the ocular blank or lens, respectively.

16. The method of claim 12, wherein altering the ocular blank or lens comprises ablating at least a portion of the blank or lens, respectively, to have a spherical power.

17. A corneal onlay produced by the method of claim 12.

18. The method of claim 12, wherein altering the lens comprises using a lathe to alter the lens.

19. The method of claim 18, wherein the lathe is used directly on the lens, or on an insert for a mold configured to form a corneal onlay.

20. The method of claim 19, wherein the lathe is used on a metal insert for a thermoplastic mold.

21. A method for enhancing vision of an individual comprising:
measuring a wavefront aberration of an eye of an individual, the eye comprising an epithelial cell layer and a Bowman's membrane;
molding a corneal onlay having an ocular power effective in correcting the vision of an eye of an individual; and
ablating a portion of the eye of the individual to correct the measured wavefront aberration to correct the wavefront aberration and wherein the posterior surface of the ocular implant is configured to substantially align with the Bowman's membrane.

22. The method of claim 21, further comprising a step of placing the corneal onlay in the eye between the epithelial cell layer and the Bowman's membrane.

23. The method of claim 22, further comprising a step of forming an epithelial flap or epithelial pocket to facilitate placement of the corneal onlay in the eye.

24. The method of claim 1, 7, 12, or 21 wherein the correction for the wavefront aberration is provided when the altered ocular implant element is located in an eye between the epithelial cell layer and the Bowman's membrane.

\* \* \* \* \*